(12) United States Patent
Li et al.

(10) Patent No.: US 6,780,620 B1
(45) Date of Patent: Aug. 24, 2004

(54) MICROBIAL TRANSFORMATION METHOD FOR THE PREPARATION OF AN EPOTHILONE

(75) Inventors: Wenying Li, Middletown, CT (US); James A. Matson, Cheshire, CT (US); Xiaohua Huang, Wallingford, CT (US); Kin Sing Lam, North Haven, CT (US); Grace A. McClure, Northford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/468,854

(22) Filed: Dec. 21, 1999

Related U.S. Application Data
(60) Provisional application No. 60/113,437, filed on Dec. 23, 1998.

(51) Int. Cl.$^7$ .......................... C12P 17/00; C12P 17/02; C12P 17/10; C12P 17/16; C12P 17/18
(52) U.S. Cl. .................. 435/117; 435/118; 435/119; 435/121; 435/123
(58) Field of Search ................... 435/117, 118, 435/119, 121, 123

(56) References Cited

U.S. PATENT DOCUMENTS

| | | | |
|---|---|---|---|
| 5,969,145 A | 10/1999 | Schinzer et al. | |
| 6,410,301 B1 * | 6/2002 | Julien et al. | 435/252.3 |
| 2003/0180760 A1 * | 9/2003 | Basch et al. | 435/6 |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/03848 | 1/1999 |
| WO | 99/07692 | 2/1999 |
| WO | WO00/31246 | 2/2000 |
| WO | WO/0039276 | 6/2000 |

OTHER PUBLICATIONS

IUBMB Enzyme Nomenclature Web Site: http://www.chem.qtnul.ac.uk/iubmb/enzyme/ECI/14/14/1.html12/1/03.*
U. Bornscheuer, Biotechnology and Bioengineering, vol. 58, No. 5, pp. 554–559, 1998.
Nicolaou et al., "Total Synthesis of 26–Hydroxy–Epothilone B and Related Analogs Via a Macrolactonization Based Strategy", Tetrahedron, 54, 7127–7166 (1998).
Nicolaou et al., "Total Synthesis of 26–Hydroxyepothilone B and Related Analogues", Chem. Commun., 24, 2343–2344 (1997).
U.S. patent application Ser. No. 08/856,533, Nicolaou et al., filed May 14, 1997.
U.S. patent application Ser. No. 08/923,869, Nicolaou et al., filed Sep. 4, 1997.
U.S. patent application Ser. No. 60/032,864, Nicolaou et al., filed Dec. 13, 1996.
Balog, A., et al., "Total Synthesis of (–)–Epothilone A", Angew. Chem. Int. Ed. Engl., vol. 35, No. 23/24, 2801–2803 (1996).
Bertini, F., et al., "Alkenes from Epoxides by Reductive Elimination with Magnesium Bromide–Magnesium Amalgam", Chem. Commun., 144 (1970).
Bollag, D.M., et al., "Epothilones, A New Class of Microtubule–stabilizing Agents with a Taxol–like Mechanism of Action", Cancer Res. 55, No. 11, 2325–2333 (1995).
Fujisawa, T., et al., "Deoxygenation of Epoxides to Olefins with FeCl$_3$—n–BuLi System", Chem. Lett., 883–886 (1974).
Fujiwara, Y., et al., "Reductive Coupling of Carbonyl Compounds to Olefins by Tungsten Hexachloride–Lithium Aluminum Hydride and Some Tungsten and Molybdenum Carbonyls", J. Org. Chem., vol. 43, No. 12, 2477–2479 (1978).
Gladysz, J. A., et al., "Deoxygenation of Epoxides by Metal Atom Cocondensation", J. Org. Chem., vol. 41, No. 22, 3647–3648 (1976).
Hofle, G., et al., "Epothilone A and B—Novel 16–Membered Macrolides with Cytotoxic Activity: Isolation, Crystal Structure, and Conformation in Solution", Angew. Chem. Int. Ed. Engl., vol. 35, No. 13/14, 1567–1569 (1996).
Hofle, G., et al., "N–Oxidation of Epothilone A–C and O–Acyl Rearrangement to C–19 and C–21—Substituted Epothilones", Angew. Chem. Int. Ed., vol. 38, No. 13/14, 1971–1974 (1999).

(List continued on next page.)

Primary Examiner—Herbert J. Lilling
(74) Attorney, Agent, or Firm—Joan Switzer; Rena Patel; Anastasia P. Winslow

(57) ABSTRACT

A microbial method for the preparation of an epothilone containing a terminal hydroxyalkyl group, comprising contacting at least one epothilone having a terminal alkyl group with an enzyme or microorganism capable of catalyzing the selective hydroxylation of said alkyl group to a hydroxyalkyl group, and effecting said hydroxylation.

21 Claims, No Drawings

OTHER PUBLICATIONS

Inokuchi, T., et al., "Opening of Epoxides to Olefins or Halohydrins with Vanadium(II)–Tetrahydrofuran or Vanadium(III)–Tetrahydrofuran Complexes", *Synlett*, No. 6, 510–512 (1992).

Kowalski. R. J., et al., "Activities of the Microtubule–stabilizing Agents Epothilones A and B with Purified Tubulin and in Cells Resistant to Paclitaxel (Taxol®)" *J. Biol. Chem.*, vol. 272, No. 4, 2534–2541 (1997).

Kupchan, S. M., et al., "Reductive Elimination of Epoxides to Olefins with Zinc–Copper Couple", *J. Org. Chem.*, vol. 36, No. 9, 1187–1190 (1971).

Martin, M. G., et al., "Epoxides as Alkene Protecting Groups. A Mild and Efficient Deoxygenation", *Tetrahedron Letters*, vol. 25, No. 3, 251–254 (1984).

McMurry, J. E., et al., "Reduction of Epoxides to Olefins with Low Valent Titanium", *J. Org. Chem.*, vol. 40, No. 17, 2555–2556 (1975).

McMurry, J. E., et al., "Some Deoxygenation Reactions with Low–Valent Titanium ($TiCl_3/LiAlH_4$)", *J. Org. Chem.*, vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", *Angew. Chem. Int. Ed. Engl.*, vol. 35, No. 20, 2399–2401 (1996).

Nicolaou, K. C., et al., "Total Synthesis of Epothilone A: The Macrolactonization Approach", *Angew. Chem. Int. Ed. Engl.*, vol. 36, No. 5, 525–527 (1997).

Nicolaou, K. C., et al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C., et al., "The Olefin Metathesis Approach to Epothilone A and Its Analogues", *J. Am. Chem. Soc.*, vol. 119, No. 34, 7960–7973 (1997).

Nicolaou, K. C., et al., "Total Syntheses of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A ans B in Solid and Solution Phase", *Nature*, vol. 387, 268–272 (1997).

Nicolaou, K. C., et al., "Synthesis of Epothilones A and B in Solid and Solution Phase" (Correction to *Nature* 387, 268–272 (1997)), *Nature*, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium ($NbCl_5/NaAlH_4$)", *Chem. Letters*, 157–160 (1982).

Schinzer, D., et al., "Total Synthesis of (–)–Epothilone A", *Angew. Chem. Int. Ed. Engl.*, vol. 36, No. 5, 523–524 (1997).

Schobert, R., et al., "Reduction and Isomerization of Oxiranes and —Diazoketones by Various Early Transition Metallocenes", *Synlett*, vol. 8, 465–466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538–6540 (1972).

Su, D.–S., et al., "Total Synthesis of (–)–Epothilone B: An Extension of the Suzuki Coupling Method and Insights into Structure–Activity Relationships of the Epothilones", *Angew. Chem. Int. Ed. Engl.*, vol. 36, No. 7, 757–759 (1997).

Su, D.–S., et al., "Structure–Activity Relationships of the Epothilones and the First In Vivo Comparison with Paclitaxel", *Angew. Chem. Int. Ed. Engl.*, vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.*, vol. 6., No. 7, 893–898 (1996).

Winkler, J. D., et al., "A Model For The Taxol (Paclitaxel)/ Epothilone Pharmacophore", *Bioorg. Med. Chem. Letts.*, vol. 6, No. 24, 2963–2966 (1996).

Yang, Z., et al., "Total Synthesis of Epothilone A: The Olefin Metathesis Approach", *Angew. Chem. Int. Ed. Engl.*, vol. 36, No. 1 / 2, 166–168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule–Stabilising Agents", *Expert Opin. Invest. Drugs*, vol. 6, No. 7, 867–873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000–8001 (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33 (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, I. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, K., et al., "Epothilons A and B: Antifungal and Cytotoxic Compounds from *Sorangiusm cellulosum* (Myxobacteria) Production, Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998–7999 (1996).

Meng, D., et al., "Total Syntheses of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidones with $MnO_2$", *J. Prakt. Chem.*, vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.*, vol. 37, No. 51, 9179–9182 (1996).

Nicolaou, K., et al., "Chemistry, Biology and Medicine of Selected Tubulin Polymerizing Agents", *Pure Appl. Chem.*, vol. 71, No. 6, 989–997 (1999).

Nicoloau, K., et al., "Total Synthesis of Epothilone E and Related Side–chain Modified Analogues Via a Stille Coupling Based Strategy", *Bioorg. Med. Chem.*, vol. 7, No. 5, 665–697 (1999).

Schinzer, D., et al., "Studies Towards the Total Synthesis of Epothilones: Asymmetric Synthesis of the Key Fragments", *Chem. Eur. J.*, vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061–2064 (1997).

Schinzer, D., et al., "Syntheses of (–)-Epothilone A", *Chem. Eur. J.*, vol. 5, No. 9, 2483–2492 (1999).

Schiner, D., et al., "Syntheses of (–)-Epothilone B", *Chem. Eur. J.*, vol. 5, No. 9, 2492–2500 (1999).

Nicolaou, K. C., et al., "Synthesis and Biological Properties of C12,13–Cyclopropylepothilone A and Related Epothilones", *Chemistry & Biology*, vol. 5, No. 7, 365–372 (1998).

* cited by examiner

MICROBIAL TRANSFORMATION METHOD FOR THE PREPARATION OF AN EPOTHILONE

This application claims priority from provisional U.S. Application Serial No. 60/113,437, filed Dec. 23, 1998, incorporated herein by reference in its entirety.

FIELD OF THE INVENTION

The present invention relates to a microbiological method for the preparation of an epothilone.

BACKGROUND OF INVENTION

Epothilones are macrolide compounds that find utility in the pharmaceutical field. For example, epothilones A and B having the structures:

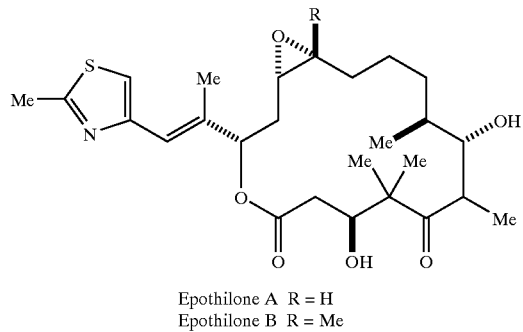

Epothilone A R = H
Epothilone B R = Me have been found to exert microtubule-stabilizing effects similar to paclitaxel (TAXOL®) and hence cytotoxic activity against rapidly proliferating cells, such as, tumor cells or other hyperproliferative cellular disease, see Bollag et al., *Cancer Res.*, Vol. 55, No. 11, 2325–2333 (1995).

Epothilones A and B are natural anticancer agents produced by *Sorangium cellulosum* that were first isolated and characterized by Hofle et al., DE 4138042; WO 93/10121; *Angew. Chem. Int. Ed. Engl.* Vol. 35, No 13/14, 1567–1569 (1996); and *J. Antibiot.*, Vol. 49, No. 6, 560–563 (1996). Subsequently, the total syntheses of epothilones A and B have been published by Balog et al., *Angew. Chem. Int. Ed. Engl.*, Vol. 35, No. 23/24, 2801–2803, 1996; Meng et al., *J. Am. Chem. Soc.*, Vol. 119, No. 42, 10073–10092 (1997); Nicolaou et al., *J. Am. Chem. Soc.*, Vol. 119, No. 34, 7974–7991 (1997); Schinzer et al., *Angew. Chem. Int. Ed. Eng.*, Vol. 36, No. 5, 523–524 (1997); and Yang et al., *Angew. Chem. Int. Ed. Engl.*, Vol. 36, No. 1/2, 166–168, 1997. PCT WO98/25929 disclosed the methods for chemical synthesis of epothilone A, epothilone B, analogs of epothilone and libraries of epothilone analogs. The structure and production from *Sorangium cellulosum* DSM 6773 of epothilones C, D, E, and F was disclosed in WO98/22461.

SUMMARY OF THE INVENTION

The present invention relate s to a method for obtaining epothilones with desired substituents at a terminal carbon position. In particular, the present invention provides a method for the preparation of hydroxyalkyl-bearing epothilones, which compounds find utility as antitumor agents and as starting materials in the preparation of other epothilone analogs.

One embodiment of the invention provides a method for the preparation of at least one epothilone of the following formula I

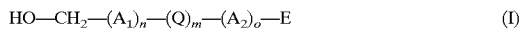

where $A_1$ and $A_2$ are independently selected from the group of optionally substituted $C_1$–$C_3$ alkyl and alkenyl;

Q is an optionally substituted ring system containing one to three rings and at least one carbon to carbon double bond in at least one ring;

n, m, and o are integers selected from the group consisting of zero and 1, where at least one of m or n or o is 1; and E is an epothilone core;

comprising the steps of contacting at least one epothilone of the following formula II

where $A_1$, Q, $A_2$, E, n, m, and o are defined as above;

with a microorganism, or an enzyme derived therefrom, which is capable of selectively catalyzing the hydroxylation of formula II, and effecting said hydroxylation.

In another embodiment, the present invention provides a method for the preparation of at least one epothilone of the following formula III:

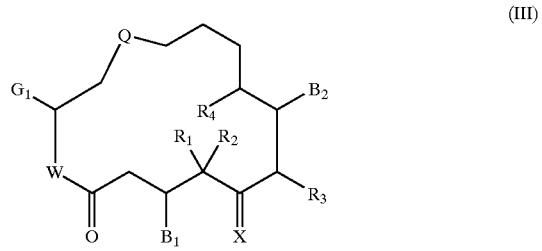

where

Q is selected from the group consisting of

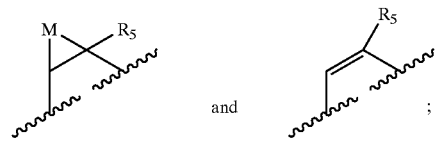

$G_1$ is the following formula V

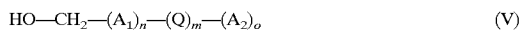

where $A_1$ and $A_2$ are independently selected from the group of optionally substituted $C_1$–$C_3$ alkyl and alkenyl;

Q is an optionally substituted ring system containing one to three rings and at least one carbon to carbon double bond in at least one ring;

n, m, and o are integers independently selected from the group consisting of zero and 1, where at least one of m or n or o is 1;

W is O or $NR_6$;

X is selected from the group consisting of O; H, $OR_7$;

M is O, S, $NR_8$, $CR_9R_{10}$;

$B_1$ and $B_2$ are selected from the group consisting of $OR_{11}$, $OCOR_{12}$;

$R_1$–$R_5$ and $R_{12}$–$R_{17}$ are selected from the group consisting of H, alkyl, substituted alkyl, aryl, and heterocyclo, and wherein when $R_1$ and $R_2$ are alkyl they can be joined to form a cycloalkyl;

$R_6$ is selected from the group consisting of H, alkyl, and substituted alkyl;

$R_7$ and $R_{11}$ are selected from the group consisting of H, alkyl, substituted alkyl, trialkylsilyl, alkyldiarylsilyl, and dialkylarylsilyl;

$R_8$ is selected from the group consisting of H, alkyl, substituted alkyl, $R_{13}C=O$, $R_{14}OC=O$ and $R_{15}SO_2$;

$R_9$ and $R_{10}$ are selected from the group consisting of H, halogen, alkyl, substituted alkyl, aryl, heterocyclo, hydroxy, $R_{16}C=O$, and $R_{17}OC=O$;

the pharmaceutically acceptable salts thereof and any hydrates, solvates, or geometric, optical and stereoisomers thereof;

comprising the steps of contacting at least one epothilone of the following formula IV:

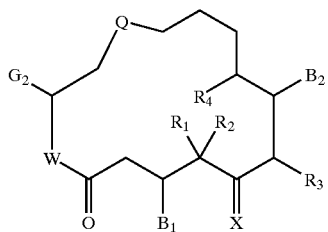

(IV)

where

Q, W, X, M, $B_1$, $B_2$, and $R_1$–$R_{17}$ are as defined above;

$G_2$ is the following formula VI

(VI)

where $A_1$, Q, $A_2$, n, m, and o are defined as above;

the pharmaceutically acceptable salts thereof and any hydrates, solvates, or geometric, optical and stereoisomers thereof;

with a microorganism or enzyme derived therefrom capable of selectively catalyzing the hydroxylation of $G_2$ to $G_1$, and effecting said hydroxylation.

DETAILED DESCRIPTION OF THE INVENTION

The present invention provides an efficient process for the preparation of epothilones having a terminal hydroxyalkyl or substituted hydroxyalkyl group from epothilones having an alkyl or substituted alkyl group at a terminal position. A single epothilone may be hydroxylated, or a mixture of different epothilones may be sequentially or simultaneously hydroxylated, according to the present invention.

All stereoconfigurations of the unspecified chiral centers of the compounds of the formulae I through VI are contemplated in the hydroxylation method of the present invention, either alone (that is, substantially free of other stereoisomers) or in admixture with other stereoisomeric forms. In the method of the present invention, the stereoconfiguration of the terminal alkyl or susbstituted alkyl group of the starting epothilone is preferably retained in the epothilone product.

Definitions

Listed below are definitions of various terms used to describe this invention. These definitions apply to the terms as they are used throughout this specification, unless otherwise limited in specific instances, either individually or as part of a larger group.

The terms "microbial process" or "microbial method," as used herein, denotes a process or method of the present invention employing a microorganism or an enzyme derived therefrom. The term "hydroxylation," as used herein, denotes the formation of a hydroxyalkyl or substituted hydroxylalkyl group from the corresponding alkyl or substituted alkyl group, and may be achieved, for example, by contact with a suitable microorganism or an enzyme.

The term "epothilone," as used herein, denotes compounds containing an epothilone core and a side chain group as defined herein. The term "epothilone core," as used herein, denotes a moiety containing the core structure (with the numbering of ring system positions used herein shown):

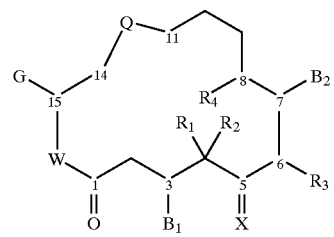

wherein the substituents are as defined herein above.

The term "side chain group" refers to substituent G as defined by $G_1$ and $G_2$ herein above.

The term "terminal carbon" or "terminal alkyl group" refers to the terminal carbon or terminal methyl group of the moiety either directly bonded to the epothilone core at position 15 or to the terminal carbon or terminal alkyl group of the side chain group bonded at position 15. It is understood that the term "alkyl group" includes alkyl and substituted alkyl as defined herein.

The term "pharmaceutically active agent" or "pharmaceutically active epothilone" refers to an epothilone that is pharmacologically active in treating cancer or other diseases described herein.

The term "alkyl" refers to optionally substituted, straight or branched chain saturated hydrocarbon groups of 1 to 20 carbon atoms, preferably 1 to 7 carbon atoms. The expression "lower alkyl" refers to optionally substituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyloxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "ring system" refers to an optionally substituted ring system containing one to three rings and at least one carbon to carbon double bond in at least one ring. Exemplary ring systems include, but are not limited to, an aryl or a partially or fully unsaturated heterocyclic ring system, which may be optionally substituted.

The term "aryl" refers to monocyclic or bicyclic aromatic hydrocarbon groups having 6 to 12 carbon atoms in the ring portion, such as phenyl, naphthyl, biphenyl and diphenyl groups, each of which may be optionally substituted.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "aralkyl" refers to an aryl group bonded directly through an alkyl group, such as benzyl.

The term "substituted alkene" and "substituted alkenyl" refer to a moiety having a carbon to carbon double bond, which can be part of a ring system, with at least one substituent being a lower alkyl or substituted lower alkyl. Other substituents are as defined for substituted alkyl.

The term "cycloalkyl" refers to a optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocyclos, such as, epoxides and aziridines.

The term "alkanoyl" refers to —C(O)-alkyl.

The term "substituted alkanoyl" refers to —C(O)-substituted alkyl.

The term "aroyl" refers to —C(O)-aryl.

The term "substituted aroyl" refers to —C(O)-substituted aryl.

The term "trialkylsilyl" refers to —Si(alkyl)$_3$.

The term "aryl dialkylsilyl" refers to —Si(alkyl)$_2$(aryl).

The term "diaryl alkylsilyl" refers to —Si(aryl)$_2$(alkyl).

The term "heteroatoms" shall include oxygen, sulfur and nitrogen.

The term "halogen" or "halo" refers to fluorine, chlorine, bromine and iodine.

The compounds of formula I through IV may form salts with alkali metals such as sodium, potassium and lithium, with alkaline earth metals such as calcium and magnesium, with organic bases such as dicyclohexylamine and tributylamine, with pyridine and amino acids such as arginine, lysine and the like. Such salts can be obtained, for example, by exchanging the carboxylic acid protons, if they contain a carboxylic acid, from compounds of formula I and II with the desired ion in a medium in which the salt precipitates or in an aqueous medium followed by evaporation. Other salts can be formed as known to those skilled in the art.

The compounds of formula I through IV form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others (e.g. nitrates, phosphates, borates, tartrates, citrates, succinates, benzoates, ascorbates, salicylates and the like). Such salts are formed by reacting a compound of formula I through IV in an equivalent amount of the acid in a medium in which the salt precipitates or in an aqueous medium followed by evaporation.

In addition, zwitterions ("inner salts") can be formed and are included within the term salts as used herein.

Prodrugs and solvates of the compounds of formula I through IV are also contemplated herein. The term prodrug, as used herein, denotes a compound which, upon administration to a subject, undergoes chemical conversion by metabolic or chemical processes to yield a compound of formula I through IV, or a salt and/or solvate thereof. For example, compounds of formula I through IV may form a carboxylate ester moiety. The carboxylate esters are conveniently formed by esterifying any of the carboxylic acid functionalities found on the disclosed ring structure(s). Solvates of the compounds of formula I through IV are preferably hydrates.

Various forms of prodrugs are well known in the art. For examples of such prodrug delivery derivatives, see:

a) *Design of Prodrugs*, H. Bundgaard (editor), Elsevier (1985);

b) *Methods in Enzymology*, K. Widder et al. (editors), Academic Press, Vol. 42, 309–396 (1985);

c) *A Textbook of Drug Design and Development*, Krosgaard-Larsen and H. Bundgaard (editors), Chapter 5, "Design and Application of Prodrugs," 113–191 (1991);

d) H. Bundgaard, *Advanced Drug Delivery Reviews*, 8, 1–38 (1992);

e) H. Bundgaard, *J. of Pharm. Sciences*, 77, 285 (1988); and f) N. Kakeya et al., *Chem. Pharm. Bull.*, 32 692 (1984).

The compounds of the invention may exist as multiple optical, geometric, and stereoisomers. While the compounds shown herein are depicted for one optical orientation, included within the present invention are all isomers and mixtures thereof.

GENERAL METHODS OF PREPARATION

In general, the hydroxyalkyl-bearing epothilone product of the invention can be produced by culturing a microorganism or enzyme, capable of selectively hydroxylating a terminal carbon or alkyl, in the presence of a suitable epothilone substrate in an aqueous nutrient medium containing sources of assimilable carbon and nitrogen, under submerged aerobic conditions.

Starting Materials

The epothilones employed as starting materials for the present invention may be any such compound having a terminal carbon or terminal alkyl group capable of undergoing the enzymatic hydroxylation of the present invention. The starting material, or substrate, can be isolated from natural sources, such as *Sorangium cellulosum*, or they can be synthetically formed epothilones.

In a preferred embodiment, the starting material is epothilone B. Epothilone B can be obtained from the fermentation of *Sorangium cellulosum* So ce90, as described in DE 41 38 042/WO 93/10-21. The strain has been deposited at the Deutsche Sammlung von Mikroorganismen (German Collection of Microorganisms) (DSM) under No. 6773. The process of fermentation is also described in Hofle, G., et al., *Angew. Chem. Int. Ed. Engl.*, Vol 35, No. 13/14, 1567–1569 (1996). Epothilone B can also be obtained by chemical means, such as those disclosed by Meng, D., et al., *J. Am. Chem. Soc.*, Vol. 119, No. 42, 10073–10092 (1996); Nicolaou, K., et al., *J. Am. Chem. Soc.*, Vol. 119, No. 34, 7974–7991 (1997) and Schinzer, D., et al., *Chem. Eur. J.*, Vol. 5, No. 9, 2483–2491 (1999).

Enzymes and Microorganisms

The enzyme or microorganism employed in the present invention may be any enzyme or microorganism capable of selectively catalyzing the enzymatic hydroxylation described herein. Specifically, the microorganism, or any enzyme derived from said microorganism, employed in the present invention may be any microorganism capable of selectively converting the terminal carbon or terminal alkyl group into a hydroxymethyl or hydroxyalkyl group. The microorganism, regardless of origin or purity, may be employed in the free state or immobilized on a support such as by physical adsorption or entrapment.

Suitable microorganisms for the selective hydroxylation process of the invention may be selected from the genera including, but not limited to, Actinomycetes, Amycolata, Amycolatopsis, Beauveria, Candida, Gilbertella, Nocardia, Pseudomonas, Saccharopolyspora, Saccharothrix and Streptomyces. Examples of microorganism species that are known to hydroxylate terminal moieties include *Beauveria basiana, Candida rugosa*, and *Pseudomonas putida*. Examples of microorganisms that have been demonstrated to selectively hydroxylate a terminal alkyl or a substituted alkyl of an epothilone include *Amycolata autotrophica* ATCC 35203 and Actinomycetes sp. strain SC 15847 PTA-1043. In a preferred embodiment of the invention the microorganism is Actinomycetes sp. strain SC 15847 PTA-1043. Actinomycetes sp. Strain SC 15847 was isolated from Bristol-Myers Squibb's soil collection. The term "PTA-1043" as used herein refers to the accession number of the American Type Culture Collection, 10801 University Blvd, Manassas, Va., the depository for the organism referred to. The Actinomycetes sp. microorganism was deposited on Nov. 9, 1999 with the ATCC under deposit number PTA-1043. The term "SC" denotes the designation given to the microorganism as part of the Squibb culture collection. The *Amycolata autotrophica* microorganism was purchased from ATCC.

The taxonomic analysis of *Amycolata autotrophica* has been described by Okazaki, T., Serizawa, N., Enokita, R., Torikata, A., and Terahara, A., *J. Antibiot.*, 36, 1176–1183 (1983) and Lechevalier, M. P., Prauser, H., Labeda, D. P., and Ruan, J.-S., *Int. J. Systemic Bacteriol.*, 36, 29–37 (1986). The *Amycolata Autotrophica* microorganism was deposited with ATCC on behalf of Sankyo Company, Ltd. on May 23, 1983.

The biologically pure microorganisms *Amycolata autotrophica* ATCC 35203 and Actinomycetes sp. strain SC 15847 PTA-1043 are microorganisms capable of carrying out the selective hydroxylation process. It should be understood that mutants of these organisms are also contemplated by the present invention, for use in the dydroxylation method described herein, such as those modified by chemical, physical (for example, X-rays) or biological means (for example, by molecular biology techniques).

Those skilled in the art can select other microorganisms for use in the present invention by use of the following protocol.

Assay for Microorganism Selection:

To a 25 ml flask containing 2 ml of transformation medium with the same composition as set forth in Example 1 below, a small aliquot (approximately 0.1 ml) of microbial culture is inoculated into this flask. The culture is incubated at 28° C. and 250 rpm on a rotary shaker for twenty four hours. To the culture is added 0.2 mg of an epothilone substrate and the culture is returned to the shaker for further incubation. At 45 and 60 hours, a 0.5 ml aliquot is removed and assayed for the formation of the hydroxyalkyl-bearing epothilone by the HPLC analysis that follows. The microorganisms found capable of carrying out the inventive process are then selected for further analysis.

Exemplary enzymes for use in the present hydroxylation are the cytochrome P-450-dependent monooxygenases isolated from microbial, mammalian and plant systems. See, H. L. Holland, *Organic Synthesis with Oxidative Enzymes*, VCH Publishers, Inc., New York, N.Y., 5–12 (1991). Enzymes may be isolated, for example, by extraction and purification methods, such as by use of hydrophobic interaction chromatography, gel filtration, followed by an anion exchange column. The present invention further provides that enzymes capable of the present selective hydroxylation method may be isolated from the genera listed above including, but not limited to, *Amycolata autotrophica* ATCC 35203 and Actinomycetes sp. strain SC 15847 PTA-1043 by the above techniques.

Where microorganisms are employed, the cells may be used in the form of intact wet cells or dried cells such as lyophilized, spray-dried or heat-dried cells, or in the form of treated cell material such as ruptured cells or cell extracts. The use of genetically engineered organisms is also contemplated. The host cell may be any cell, e.g. *Escherichia coli*, modified to contain a gene or genes for expressing one or more enzymes capable of catalysis as described herein.

Where one or more microorganisms are employed, the enzymatic hydroxylation method of the present invention may be carried out subsequent to the fermentation of the microorganism (two-stage fermentation and hydroxylation), or concurrently therewith, that is, in the latter case, by in situ fermentation and hydroxylation (single-stage fermentation and hydroxylation).

The microorganisms or enzymes used herein can be prepared by known means. See, for example, J. C. Hunter-Cevera, M. E. Fonda, and A. Belt, Chapter 1: "Isolation of Cultures," *Manual of Industrial Microbiology and Biotechnology*, edited by A. L. Demain and N. A. Solomon, American Society for Microbiology, Washington, D.C., 3–23 (1986).

The inoculum size, i.e. the amount of microorganism employed relative to the volume of the reaction mixture, is selected to allow catalysis of the enzymatic hydroxylation of the present invention. It is preferred to obtain yields in excess of 20%. Typically, to carry out the process, the inoculum size employed ranges from 1% to 20% of the reaction mixture. Preferably, the inoculum size is 2%.

Fermentation Medium

Growth of the microorganism selected for use in the process may be achieved by one of ordinary skill in the art by the use of appropriate nutrient medium. Appropriate media for the growing of microorganisms include those that provide nutrients necessary for the growth of microbial cells. See, for example, T. Nagodawithana and J. M. Wasileski, Chapter 2: "Media Design for Industrial Fermentations," *Nutritional Requirements of Commercially Important Microorganism*, edited by T. W. Nagodawithana and G. Reed, Esteekay Associates, Inc., Milwaukee, Wis., 18–45 (1998); T. L. Miller and B. W. Churchill, Chapter 10: "Substrates for Large-Scale Fermentations," *Manual of Industrial Microbiology and Biotechnology*, edited by A. L. Demain and N. A. Solomon, American Society for Microbiology, Washington, D.C., 122–136 (1986). A typical medium for growth includes necessary carbon sources, nitrogen sources, and trace elements. Inducers may also be added to the medium. The term inducer as used herein, includes any compound enhancing formation of the desired enzymatic activity within the microbial cell. Typical inducers as used herein may include solvents used to dissolve substrates, such as dimethyl sulfoxide, dimethyl formamide, dioxane, ethanol and acetone. Further, some substrates, such as epothilone B, may also be considered to be inducers.

Carbon sources may include sugars such as glucose, fructose, galactose, maltose, sucrose, mannitol, sorbital, glycerol starch and the like; organic acids such as sodium acetate, sodium citrate, and the like; and alcohols such as ethanol, propanol and the like. Preferred carbon sources include, but are not limited to, glucose, fructose, sucrose, glycerol and starch.

Nitrogen sources may include an N-Z amine A, corn steeped liquor, soybean meal, beef extract, yeast extract, tryptone, peptone, cottonseed meal, peanut meal, amino acids such as sodium glutamate and the like, sodium nitrate, ammonium sulfate and the like.

Trace elements may include magnesium, manganese, calcium, cobalt, nickel, iron, sodium and potassium salts. Phosphates may also be added in trace or preferably, greater than trace amounts.

The medium employed for the fermentation may include more than one carbon or nitrogen source or other nutrient Preferred medium for growth includes aqueous media, particularly that which is described in the Examples herein. Preferably the hydroxylation process of the present invention is carried out under submerged aerobic conditions.

For growth of the microorganisms and/or hydroxylation according to the method of the present invention, the pH of the medium is preferably from about 5 to about 8 and the temperature is from about 24° C. to about 37° C., preferably the temperature is 28° C.

The aqueous medium is incubated for a period of time necessary to complete the biotransformation as monitored by high pressure liquid chromatography (HPLC). Typically, the period of time needed to complete the transformation is twelve to sixty hours and preferably about 45 hours after the addition of the substrate. The medium is placed on a rotary shaker (New Brunswick Scientific Innova 5000) operating at 150 to 300 rpm and preferably about 250 rpm with a throw of 2 inches.

Separation and Isolation

The hydroxyalkyl-bearing product can be recovered from the fermentation broth by conventional means that are commonly used for the recovery of other known biologically active substances. Examples of such recovery means include, but are not limited to, isolation and purification by extraction with a conventional solvent, such as ethyl acetate and the like; by pH adjustment; by treatment with a conventional resin, for example, by treatment with an anion or cation exchange resin or a non-ionic adsorption resin; by treatment with a conventional adsorbent, for example, by distillation, by crystallization; or by recrystallization, and the like.

The extract obtained above from the biotransformation reaction mixture can be further isolated and purified by gradient elution column chromatography and analytical thin layer chromatography. The protocol for the extraction of the product of the examples that follow is set forth below.

Gradient Elution Chromatography:

All column chromatography was carried out using a 1.5 cm (internal diameter)×20 cm length Spectra/Chrom™ column purchased from Spectrum Medical Industries, Los Angeles, Calif. The column was slurry packed for each experiment. Approximately 16 g of silica gel (63–200 um, 70–230 mesh, purchased from EM Separations, New Jersey) was slurried in 75 to 100 ml of hexane or toluene and added to the column in a single pour. The bed was allowed to form and pack under maximum gravity flow. Samples were absorbed onto the silica gel before applying to the packed column. Linear gradients were formed using a Spectrum gradient elution apparatus which consisted of two 500 ml chambers.

Analytical Thin Layer Chromatography (TLC):

Aliquots (9 μl) of column fractions were spotted to Uniplate Silica Gel GHLF precoated thin layer chromatography plates (scored, 10×20 cm, 250 micron thickness, purchased from Analtech, Inc., Newark, Del.) using 3 μl Microcaps™ disposable pipettes. Spotted plates were developed in filter paper lined tanks equilibrated with the specified eluants. After spraying the developed plates with vanillin (99 parts 2% (w/v) vanillin/ethanol—1 part concentrated sulfuric acid), the compounds were visualized with gentle heating.

Use and Utility

The invention is a process by which compounds that are microtubule-stabilizing agents are produced. The compounds, and thus the process, are useful in the treatment of a variety of cancers and other proliferative diseases including, but not limited to, the following;

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seninoma, tetratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer and teratocarcinoma.

Compounds produced by the invention will also inhibit angiogenesis, thereby affecting the growth of tumors and providing treatment of tumors and tumor-related disorders. Such anti-angiogenesis properties of the compounds of formula I and II will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Compounds produced by the invention will induce or inhibit apoptosis, a physiological cell death process critical for normal development and homeostasis. Alterations of apoptotic pathways contribute to the pathogenesis of a variety of human diseases. Compounds of formula I and II, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Without wishing to be bound to any mechanism or morphology, compounds produced by the invention may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The present invention thus provides a method of treating a subject, preferably mammals and especially humans, in need of treatment for any of the aforementioned conditions, especially cancer or other proliferative diseases, comprising the step of administering to a subject in need thereof of at least one compound of formula I and II in an amount effective therefor. Other therapeutic agents such as those described below may be employed with the inventive compounds in the present method. In the method of the present invention, such other therapeutic agent(s) may be administered prior to, simultaneously with or following the administration of the compound(s) of the present invention.

The effective amount of a compound produced by the present invention may be determined by one of ordinary skill in the art, and includes exemplary dosage amounts for a human of from about 0.05 to 200 mg/kg/day, which may be administered in a single dose or in the form of individual divided doses, such as from 1 to 4 times per day. Preferably the compounds are administered in a dosage of less than 100 mg/kg/day, in a single dose or in 2 to 4 divided doses. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The present invention also provides compounds for a pharmaceutical composition comprising at least one of the compounds produced by the invention capable of treating cancer or other proliferative diseases in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds produced by the invention may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as a tablet, capsule, solution or suspension containing about 5 to about 500 mg per unit dosage of a compound or mixture of compounds produced by the invention or in a topical form (0.01 to 5% by weight compound, one to five treatments per day). They may be compounded in a conventional manner with a physiologically acceptable vehicle or carrier, excipient, binder, preservative, stabilizer, flavor, etc., or with a topical carrier.

The compounds of the invention can also be formulated in compositions such as sterile solutions or suspensions for parenteral administration. About 0.1 to 500 mg of a compound produced by the invention may be compounded with a physiologically acceptable vehicle, carrier, excipient, binder preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, buffering agents, solubilizers and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parentally acceptable diluents or solvents, such as cremophor, mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperature, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat plaques associated with psoriasis and as such may be formulated as a cream or ointment.

The compounds of the invention may be administered either alone or in combination with other anti-cancer and cytotoxic agents and treatments useful in the treatment of cancer or other proliferative diseases. Especially useful are anti-cancer and cytotoxic drug combinations wherein the second drug chosen acts in a different manner or different phase of the cell cycle, e.g. S phase, than the present compounds of formula I and II which exert their effects at the $G_2$-M phase. Example classes of anti-cancer and cytotoxic agents include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; cyclin dependent kinase inhibitors, such as flavopyridol; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®); plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compounds of the invention may also be used in conjunction with radiation therapy.

Representative examples of these classes of anti-cancer and cytotoxic agents include, but are not limited to, mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Examples of anti-cancer and other cytotoxic agents include the following: epothilone derivatives as found in German Patent No. 4138042.8; WO 97/19086, WO 98/22461, WO 98/25929, WO 98/38192, WO 99/02224, WO 99/02514, WO 99/03848, WO 99/07692, WO99/27890, and WO 99/28324; cyclin dependent kinase inhibitors as found in WO 99/24416; and prenyl-protein transferase inhibitors as found in WO 97/30992 and WO 98/54966.

The combinations of the present invention may also be formulated or co-administered with other therapeutic agents that are selected for their particular usefulness in administering therapies associates with the aforementioned conditions. For example, the compounds of the invention may be formulated with agents to prevent nausea, hypersensitivity, and gastric irritation, such as a $H_1$ and $H_2$ antihistaminics.

The above therapeutic agents, when employed in combination with the compounds of the present invention, may be used in those amounts indicated in the Physicians' Desk Reference (PDR) or as otherwise determined by one of ordinary skill in the art.

Preferred Compounds

In a preferred embodiment of the present invention, epothilone F is obtained by the fermentation of epothilone B with the microorganism *Amycolata autotrophica* ATCC 35203. Epothilone B and F are antitumor agents useful in the treatment of cancers in humans and have the following chemical structures:

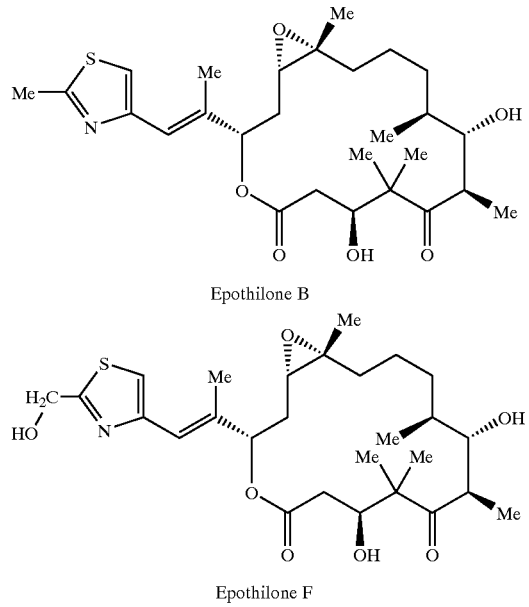

Epothilone B

Epothilone F

In another preferred embodiment of the invention, epothilone F is obtained by the fermentation of epothilone B with the microorganism Actinomycetes sp. strain SC15847 PTA-1043.

While epothilone B and epothilone F can in and of themselves be used as the final end product, i.e. as pharmaceutically active agents, the invention contemplates that the epothilone product of the present process can be employed to prepare other pharmaceutically active epothilones, or derivatives or analogs thereof. For example, the epothilone product of the present process can be used to prepare the epothilone analogs described in DE 199 07 588.3, the text of which is incorporated herein as if set forth at length, or the examples set forth herein, in which epothilone F is employed as the starting material or intermediate.

In a preferred embodiment of the invention, the process is used to prepare epothilones having lower hydroxyalkyl or lower substituted hydroxyalkyl substituents.

In a preferred embodiment of the invention, in formulas I and III, n is zero and m is 1. In a more preferred embodiment, in formulas I and III, n is zero, m is 1, and $A_2$ is alkenyl.

Those skilled in the art would be able to optimize the culture conditions, including inoculum size, the composition of the medium, reaction conditions such as temperature, aeration, agitation, pH and time, solvents used to dissolve the substrate, and concentrations using known methods and the general methods of preparation described herein.

All references cited herein with respect to synthetic, preparative and analytic procedures are incorporated by reference as if set forth at length herein.

The following examples are provided for the purpose of illustrating the present invention and should not be construed as being a limitation on the scope or spirit of the instant invention.

EXAMPLE 1

Biotransformation of Epothilone B to Epothilone F
Microorganism and Culture Conditions A frozen vial (approximately 2 ml) of *Amycolata autotrophica* ATCC 35203 was used to inoculate a 500 ml flask containing 100 ml of the transformation medium. The transformation medium consisted of 10 g of dextrose (Em Science, Gibbstown, N.J.), 5.0 g of polypeptone, 3.0 g of yeast extract (Difco, Detroit, Mich.) and 3.0 g of malt extract (Difco, Detroit, Mich.) in one liter of deionized water. Ten flasks were inoculated and the cultures were incubated at 28° C. and 250 rpm for 24 hours. A total of 840 ml of the resulting culture was combined in a two liter flask, to which 610 mg of the substrate, epothilone B, in 25 ml ethanol was added. The culture was then divided into forty-two 250 ml flasks (about 20 ml culture per flask) and incubated at 28° C. and 250 rpm. The conversion of epothilone B to epothilone F in the culture was monitored by HPLC to determine the time that no additional production of epothilone F was observed. The maximum conversion yield was obtained at around 45 hours after the addition of epothilone B to the culture.

Isolation and Purification of [1S-[1R*,3R*(E),7R*,10S*,11R*,12R*,16S*]]-7,11-Dihydroxy-8,8,10,12,16-pentamethyl-3-[1-methyl-2-(2-hydroxymethyl-4-thiazolyl)ethenyl]-4,17-dioxabicyclo[14.1.0]heptadecane-5,9-dione)

The above biotransformation reaction culture was rinsed into a four liter beaker with deionized water to yield approximately two liters of liquid. The rinsed reaction liquid was vigorously mixed with two liters of ethyl acetate using a magnetic stirrer. After two hours approximately 500 ml of filter aid Dicalite (diatomaceous earth, Grefco Minerals, Torrance Calif.) was added and the resulting mixture was filtered. The filtrate was transferred to a six liter separatory funnel and upon phase separation, the lower aqueous layer was discarded. The upper organic phase was concentrated to dryness in a rotary evaporator to give a crude extract.

The crude extract was then subjected to column chromatography using a one liter linear gradient of hexane to 50% acetone in hexane. A total of twenty 50 ml fractions were collected. After TLC analysis, fractions 10 and 11 were pooled and evaporated to yield 88 mg of epothilone B. Fraction 15 was evaporated to yield 71 mg of epothilone F. Fractions 16 and 17 were pooled and evaporated to give a mixture of epothilone F and 26-hydroxyepothilone B (130.3 mg). The total synthesis of 26-hydroxyepothilone B has previously been reported (K. C. Nicolaou et al., *Tetrahedron*, 54, 7127–7166 (1998)).

The mixture of epothilone F and 26-hydroxyepothilone B was purified further by column chromatography using a one liter linear gradient of hexane to 80% ethyl acetate in hexane. A total of forty 25 ml fractions were collected. After TLC analysis, fractions 14 to 19 were pooled and evaporated to give 55.4 mg of epothilone F. Fractions 20 to 25 were pooled and evaporated to give 26-hydroxyepothilone B contaminated with a small amount of epothilone F.

The latter mixture of epothilone F and 26-hydroxyepothilone B was refined further by column chromatography using a 700 ml gradient of toluene to 35% acetone in toluene. A total of twenty 35 ml fractions were collected. TLC analysis showed that fractions 14 and 15contained pure epothilone F, while fractions 18 through 20 contained pure 26-hydroxyepothilone B. The total yield of epothilone F, calculated from the amount of epothilone F recovered (126.4 mg) to the amount of starting substrate, epothilone B (610 mg), was 20.7%.

EXAMPLE 2

Biotransformation of Epothilone B to Epothilone F
Microorganism and Culturing Conditions A frozen vial (approximately 2 ml) of Actinomycetes sp. strain PTA-1043 was used to inoculate a 500 ml flask containing 100 ml of the medium. The vegetative medium consists of 20 g of dextrose (EM Science, Gibbstown, N.J.), 10 g of malt extract (Difco, Detroit, Mich.), 10 g of yeast extract (Difco, Detroit, Mich.) and 1 g of peptone (Difco, Detroit, Mich.) in liter of deionized water. The vegetative culture was the resulting culture was added to each of sixty-two 500 ml flasks containing the transformation medium which has the same composition as the vegetative medium. The cultures were incubated at 28° C. and 250 rpm for 24 hours. Epothilone B (4.96 g) was dissolved in 155 ml of ethanol and the solution was distributed to the sixty-two flasks. The flasks were then returned to the shaker and incubated for an additional 43 hours at 28° C. and 250 rpm. The reaction culture was then processed for the recovery of epothilone F.

Isolation and Purification of [1S-[1R*,3R*(E),7R*,10S*,11R*,12R*,16S*]]-7,11-Dihydroxy-8,8,10,12,16-pentamethyl-3-[1-methyl-2-(2-hydroxymethyl-4-thiazolyl)ethenyl]-4,17-dioxabicyclo[14.1.0]heptadecane-5,9-dione)

The above biotransformation reaction culture was rinsed into a ten liter polypropylene bucket with deionized water to yield approximately four liters of liquid. The rinsed reaction liquid was vigorously stirred with four liters of ethyl acetate. After one hour of mixing, approximately one liter of filter aid Dicalite (diatomaceous earth, Grefco Minerals, Torrance Calif.) was added and the resulting mixture was filtered onto a bed of filter aid (Dicalite, Grefco Minerals, Torrance Calif.). The filtrate was transferred to a twenty liter separatory funnel and the phases were allowed to separate. The solids were extracted once with four liters of acetone and filtered. The aqueous-acetone filtrate was concentrated to approximately one liter and extracted three times with one liter aliquots of ethyl acetate. All of the ethyl acetate extracts were pooled and concentrated to dryness under vacuum to yield 6.7 g of residue. This residue was pre-absorbed onto 6 g of silica gel and subjected to column, chromatography (60 g silica gel, 2.5 cm i.d.×30 cm length Spectra/Chrom column fitted with an adjustable end fitting). The column was eluted with a two liter linear gradient of hexane to 50% acetone in hexane. A total of twenty 100 ml fractions were collected. After TLC, fractions 13 to 20 were pooled and evaporated to yield 1.65 g epothilone F. The total yield of epothilone F, calculated from the amount of epothilone F recovered (1.65 g) to the amount of starting substrate, epothilone B (4.96 g) was 33.3%.

EXAMPLE 3

The following syntheses provide examples where the hydroxyalkyl-bearing product of the invention has been used as an intermediate or as the starting material to prepare other epothilone analogs or derivatives. Epothilone analogs or derivatives prepared from hydroxyalkyl-bearing epothilones are disclosed in DE 19907588.3, the text of which is incorporated herein as if set forth at length.

A. Synthesis of [1S-[1R*,3R*(E),7R*,10S*,11R*,12R*,16S*]]-7,11-Dihydroxy-8,8,10,12,16-pentamethyl-3-[1-methyl-2-(2-azidomethyl-4-thiazolyl)ethenyl]-4,17-dioxabicyclo[14.1.0]heptadecane-5,9-dione To a stirred solution of epothilone F (957 mg, 1.828 mmol) in 20.0 ml of tetrahydrofuran at 0° C. under Argon was added 0.47 ml of diphenylphosphoryl azide (604 mg, 2.194 mmol, 1.2 equivalents). The mixture was stirred for about three minutes, 1,8-Diazabicyclo[5.4.0]undec-7-ene (0.27 ml, 278 mg, 1.828 mmol, 1 equivalents) was then added and the resulting mixture was stirred at 0° C. After two hours, the mixture was warmed to 25° C. and stirred for an additional twenty hours. The reaction mixture was diluted with 150 ml ethyl acetate and washed with 50 ml of water. The aqueous layer was extracted with 35 ml ethyl acetate. The combined organic layers were dried over $Na_2SO_4$ and concentrated under vacuum. The crude material was chromatographed using silica gel eluted with 50% ethyl acetate in hexane to afford 913 mg (91%) of 21-azido-epothilone B, as a clear, colorless oil.

MS (ESI+): 549.3 (M+H)+.

B. Synthesis of [1S-[1R*,3R*(E),7R*,10S*,11R*,12R*,16S*]]-7,11-Dihydroxy-8,8,10,12,16-pentamethyl-3-[1-methyl-2-(2-aminomethyl-4-thiazolyl)ethenyl]-4,17-dioxabicyclo[14.1.0]heptadecane-5,9-dione To a stirred solution of the azide product (from section A above) (1.070 g, 1.950 mmol) in 30.0 ml of tetrahydrofuran under Argon was added 0.22 ml of trimethylphosphine (0.163 g, 2.145 mmol, 1.1 equivalent) and 5.5 ml of water. T mixture was allowed to stir at room temperature for three hours. The azide was completely consumed and 3 ml of 28% $NH_4OH_{(aq)}$ was added to complete the conversion of phosphorylimine to amine. After stirring at room for one hour the solvent(s) was removed under vacuum. The crude material was chromatographed using silica gel eluting with 1% $Et_3N$, 2.5% MeOH in $CHCl_3$ to yield 924 mg (91% a white solid.

In addition to the epothilone analogs and derivatives named above, the following compounds can be made from the hydroxylalkyl-bearing epothilones of present invention:

[1S-[1R*,3R*(E),7R*,10S*,11R*,12R*,16S*]]-7,11-Dihydroxy-8,8,10,12-tetramethyl-3-[1-methyl-2-(2-n-propionylaminomethyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-n- pentanoylaminomethyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-chloromethyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-Dihydroxy-8,8,10,12-tetramethyl-3-[1-methyl-2-(2-aminomethyl-4-thiazolyl)ethenyl]-4,17-dioxabicyclo[14.1.0]heptadecane-5,9-dione.

[1S-[1R*,3R*(E),7R*,10S*,11R*,12R*,16S*]]-7,11-Dihydroxy-8,8,10,12-tetramethyl-3-[1-methyl-2-(2-azidomethyl-4-thiazolyl)ethenyl]-4,17-dioxabicyclo[14.1.0]heptadecane-5,9-dione; and

[1S-[1R*,3R*(E),7R*,10S*,11R*,12R*,16S*]]-7,11-Dihydroxy-8,8,10,12-tetramethyl-3-[1-methyl-2-(2-hydroxymethyl-4-thiazolyl)ethenyl]-4,17-dioxabicyclo[14.1.0]heptadecane-5,9-dione.

EXAMPLE 4

Characterization of Epothilone F

Epothilone F of this invention was identified by NMR spectroscopy and has the following characteristics:

| Description: | White crystalline solid |
|---|---|
| Melting point: | 141–143 C |
| Molecular Formula: | $C_{27}H_{41}NO_7S$ |
| Molecular Weight: | 523 |
| NMR: | Observed Chemical Shifts |
| | Solvent CDCl3 (7.24, 77.0) |
| | Bruker DRX-500: proton 500.13 MHz, carbon 125.76 MHz |

| Position | Proton | Pattern | C-13 |
|---|---|---|---|
| 1 | — | — | 170.5 |
| 2 | 2.45 | m | 39.19 |
| 2 | 2.30 | m | — |
| 3 | 4.12 | d, J = 9.3 | 73.00 |
| 4 | — | — | 52.95 |
| 5 | — | — | 170.20 |
| 6 | 3.21 | m | 43.10 |
| 7 | 3.68 | m | 74.31 |
| 8 | 1.63 | m | 36.41 |
| 9 | 1.35 | m | 31.22 |
| 10 | 1.37 | m | 32.20 |
| 11 | 1.63 | m | 30.74 |
| 11 | 1.37 | m | — |
| 12 | — | — | 31.34 |
| 13 | 2.72 | m | 61.54 |
| 14 | 1.99 | m | 31.99 |
| 14 | 1.86 | m | — |
| 15 | 5.36 | m | 77 |
| 16 | — | — | 137.72 |
| 17 | 6.52 | s | 119.50 |
| 18 | — | — | 152.17 |
| 19 | 7.03 | s | 116.92 |
| 20 | — | — | 170.20 |
| 21 | 4.83 | s | 62.01 |
| 22 | 1.30 | s | 22.50 |
| 23 | 0.99 | s | 21.36 |
| 24 | 1.08 | d, J = 6.90 | 13.80 |
| 25 | 0.92 | d, J = 6.65 | 17.11 |
| 26 | 1.20 | s | 22.74 |
| 27 | 2.00 | s | 15.74 |
| 3-OH | 3.98 | s | — |

We claim:

1. A method for the preparation of at least one hydroxyalkyl-bearing compound of the following formula III:

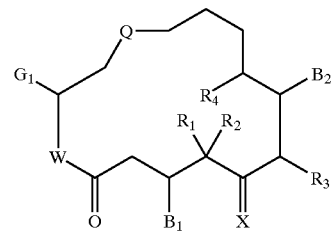
(III)

where
Q is selected from the group consisting of

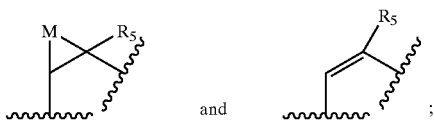
and ;

$G_1$ is the following formula V $$HO-CH_2-(A_1)_n-(Q_1)_m-(A_2)_o$$ (V), where
$A_1$ and $A_2$ are independently selected from the group of optionally substituted $C_1-C_3$ alkyl and alkenyl;
$Q_1$ is an optionally substituted ring system containing one to three rings and at least one carbon to carbon double bond in at least one ring;
n, m, and o are integers independently selected from the group consisting of zero and 1, where at least one of m or n or o is 1;
W is O or $NR_6$;
X is selected from the group consisting of O and H, $OR_7$;
M is O, S, $NR_8$, or $CR_9R_{10}$;
$B_1$ and $B_2$ are selected from the group consisting of $OR_{11}$, and $OCOR_{12}$;
$R_1-R_5$ and $R_{12}-R_{17}$ are selected from the group consisting of H, alkyl, substituted alkyl, aryl, and heterocyclo, and wherein when $R_1$ and $R_2$ are alkyl they can be joined to form a cycloalkyl;
$R_6$ is selected from the group consisting of H, alkyl, and substituted alkyl;
$R_7$ and $R_{11}$ are selected from the group consisting of H, alkyl, substituted alkyl, trialkylsily, alkyldiarylsilyl, and dialkylarylsilyl;
$R_8$ is selected from the group consisting of H, alkyl, substituted alkyl, $R_{13}C=O$, $R_{14}OC=O$ and $R_{15}SO_2$;
$R_9$ and $R_{10}$ are selected from the group consisting of H, halogen, alkyl, substituted alkyl, aryl, heterocyclo, hydroxy, $R_{16}C=O$, and $R_{17}OC=O$;
the pharmaceutically acceptable salts thereof and any hydrates, solvates, or geometric, optical and stereoisomers thereof;
comprising the steps of contacting at least one compound of the following formula IV:

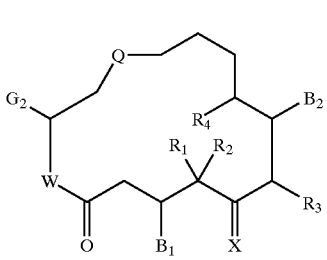
(IV)

where

Q, W, X, M, $B_1$, $B_2$, and $R_1$–$R_{17}$ are as defined above;
$G_2$ is the following formula VI $$CH_3-(A_1)_n-(Q_1)_m-(A_2)_o \qquad (VI),$$

where $A_1$, $Q_1$, $A_2$, n, m, and o are defined as above;

the pharmaceutically acceptable salts thereof and any hydrates, solvates, or geometric, optical and stereoisomers thereof;

with a microorganism, or P-450 enzyme isolated therefrom, said microorganism or P-450 enzyme capable of selectively catalyzing the hydroxylation of $G_2$ to $G_1$ and effecting said hydroxylation.

2. The method of claim 1 wherein said compound of formula III is epothilone F and said compound of formula IV is epothilone B.

3. The method of claim 1 wherein n is zero and m is 1.

4. The method of claim 1 wherein n is zero, m is 1, and $A_2$ is alkenyl.

5. The method of claim 1 wherein said microorganism is selected from the group consisting of Actinomycetes, Amycolata, Amycolatopsis, Beauveria, Candida, Gilbertella, Nocardia, Pseudomonas, Saccharopolyspora, Saccharothrix and Streptomyces.

6. The method of claim 1 wherein said microorganism is selected selected from the group consisting of *Amycolata autotrophica, Beauveria basiana, Candida rugosa*, and *Pseudomonas putida*.

7. The method of claim 1 wherein said microorganism is selected from the group consisting of *Amycolata autotrophica* ATCC 35203 and Actinomycetes sp. strain SC 15847 PTA-1043.

8. The method of claim 1, wherein said microorganism is Actinomycetes sp. strain SC 15847 PTA-1043.

9. The method of claim 1 wherein said method comprises a biotransformation under submerged aerobic conditions in an aqueous medium.

10. The method of claim 9, wherein said aqueous medium contains carbon and nitrogen nutrients at approximately pH 5–8.

11. The method of claim 1, wherein said P-450 enzyme is isolated from a microorganism selected from the group consisting of Actinomycetes, Amycolata, Amycolatopsis, Beauveria, Candida, Gilbertella, Nocardia, Pseudomonas, Saccharopolyspora, Saccharothrix and Streptomyces.

12. The method of claim 1 wherein said P-450 enzyme is isolated from a microorganism selected from the group consisting of *Amycolata autotrophica* ATCC 35203 and Actinomycetes sp. strain SC 15847 PTA-1043.

13. The method of claim 1, wherein $G_1$ is

14. The method of claim 1, wherein $G_2$ is

15. The method of claim 1, wherein Q is

16. The method of claim 1, wherein Q is

17. The method of claim 1, wherein the compound of formula (III) is a compound having the formula, wherein W is O or NH.

18. The method of claim 17, wherein $G_1$ is

19. The method of claim 14, wherein $G_2$ is

20. The method of claim 17, wherein Q is

21. The method of claim 17, wherein Q is

* * * * *

UNITED STATES PATENT AND TRADEMARK OFFICE
CERTIFICATE OF CORRECTION

PATENT NO. : 6,780,620 B1 Page 1 of 1
DATED : August 24, 2004
INVENTOR(S) : Li et al.

It is certified that error appears in the above-identified patent and that said Letters Patent is hereby corrected as shown below:

Column 22,
Line 41, "A method of claim 14," should read -- A method of claim 17, --

Signed and Sealed this

Seventh Day of December, 2004

JON W. DUDAS
*Director of the United States Patent and Trademark Office*